United States Patent [19]
Bartmann et al.

[11] Patent Number: 5,635,107
[45] Date of Patent: Jun. 3, 1997

[54] FLUORINE-CONTAINING FIVE-MEMBERED RING COMPOUNDS, AND A LIQUID-CRYSTALINE MEDIUM CONTAINING THEM

[75] Inventors: Ekkehard Bartmann; Georg Weber, both of Erzhausen, Germany

[73] Assignee: Merck Patent Gesellschaft mit beschrankter Haftung, Darmstadt, Germany

[21] Appl. No.: 1,984

[22] Filed: Jan. 8, 1993

[30] Foreign Application Priority Data

Jan. 11, 1992 [DE] Germany .................. 42 00 524

[51] Int. Cl.$^6$ .................. C09K 19/34; C09K 19/32; C07D 307/78; C07D 236/52
[52] U.S. Cl. .................. 252/299.61; 252/299.62; 252/299.01; 549/470; 549/455; 549/456; 549/462; 549/468; 549/469; 548/217
[58] Field of Search ............. 252/299.61, 299.62, 252/299.01; 549/455, 456, 462, 468, 469, 470; 548/217

[56] References Cited

U.S. PATENT DOCUMENTS

| | | | |
|---|---|---|---|
| 4,772,730 | 9/1988 | Seelye et al. | 549/470 |
| 5,175,184 | 12/1992 | Tomiyama et al. | 514/443 |
| 5,190,690 | 3/1993 | Takiguchi et al. | 252/299.61 |
| 5,194,177 | 3/1993 | Nohira et al. | 252/299.61 |
| 5,236,619 | 8/1993 | Iwaki et al. | 252/299.61 |
| 5,244,596 | 9/1993 | Takaguchi et al. | 252/299.61 |
| 5,284,599 | 2/1994 | Iwaki et al. | 252/299.61 |
| 5,354,501 | 10/1994 | Nakamura et al. | 252/299.62 |

FOREIGN PATENT DOCUMENTS

| | | |
|---|---|---|
| 0499252 | 8/1992 | European Pat. Off. . |
| 4253789 | 9/1992 | Japan . |
| 5039482 | 2/1993 | Japan . |

*Primary Examiner*—C. H. Kelly
*Attorney, Agent, or Firm*—Millen, White, Zelane, & Branigan, P.C.

[57] ABSTRACT

Fluorine-containing five-membered ring compounds of the formula I $$R^1-(A^1-Z^1)_m-A^2-Z^2-W \qquad I$$

in which
W is

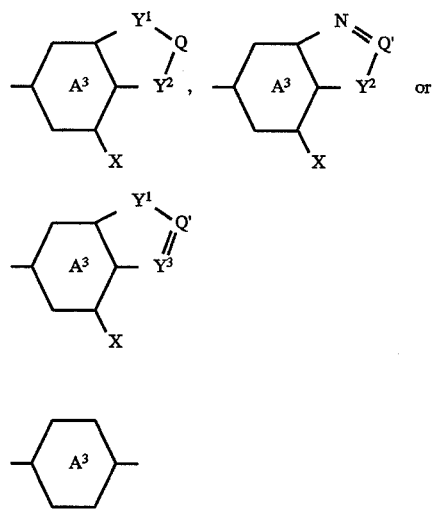

is a cyclohexane, cyclohexene or phenyl,
$Y^1$ is O or S,
$Y^2$ is (a) O, S, C=O or fluoroalkyl,
$Y^3$ is (a) N, CH or CF,
Q is C=O, CHF, CF$_2$, CHR$^2$ or CFR$^2$
Q' is CF or CR$^2$,
$R^2$ is C$_{1-15}$-alkyl, optionally at least mono-substituted by F,
X is H, F or Cl,
$R^1$ H or hydrocarbyl,
$A^1$ and $A^2$ are a carbocyclic, aromatic or heterocyclic radical
$Z^1$ and $Z^2$ are —CO—O, —O—CO—, —CH$_2$O—, —O—CH$_2$—, —CH$_2$CH$_2$—, —CH=CH—, —C≡C— or a single bond, and
m is 0, 1 or 2, and liquid-crystalline media containing same.

10 Claims, No Drawings

FLUORINE-CONTAINING FIVE-MEMBERED RING COMPOUNDS, AND A LIQUID-CRYSTALINE MEDIUM CONTAINING THEM

SUMMARY OF THE INVENTION

The invention relates to novel fluorine-containing five-membered ring compounds of the formula I

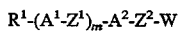

in which
W is

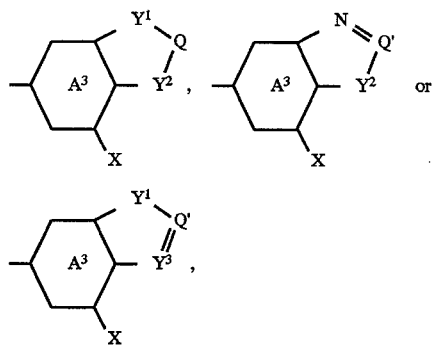

or

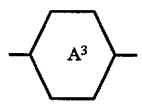

is a cyclohexane, cyclohexene or phenyl ring, $Y^1$ is O or S,
$Y^2$ is O, S, C=O or $CH_nF_{2-n}$,
n is 0, 1 or 2,
$Y^3$ is N, CH or CF,
Q is C=O, CHF, $CF_2$, $CHR^2$ or $CFR^2$,
Q' is CF or $CR^2$,
$R^2$ is an alkyl radical having 1–15 carbon atoms which is unsubstituted or at least monosubstituted by F, e.g., substituted 1, 2 or 3 times per carbon atom, e.g., perfluoro,
if Q is C=O, CHF or $CF_2$, $Y^2$ may alternatively be $CHR^2$ or $CFR^2$,
if Q' is CF $Y^3$ may alternatively be $CR^2$,
X is H, F or Cl,
$R^1$ is H, an alkyl or alkenyl radical having 1–15 carbon atoms which is unsubstituted, monosubstituted by CN or $CF_3$ or at least monosubstituted by halogen, e.g., substituted 1, 2 or 3 times per carbon atom, e.g., per halo, more preferably up to nine times per radical, it also being possible for one or more $CH_2$ groups in these radicals to be replaced, in each case independently of one another, by —O—, —S—, —CO,

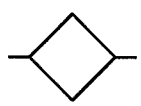

—CO—O—, —O—CO— or —O—CO—O— in such a manner that heteroatoms are not linked directly to one another, preferably no more than 3 $CH_2$ groups being replaced, $A^1$ and $A^2$, in each case independently of one another, are
a) a trans-1,4-cyclohexylene radical in which, in addition, one or more, preferably one or 2 non-adjacent $CH_2$ groups may be replaced by —O— and/or —S—,
b) a 1,4-phenylene radical in which, in addition, one or two CH groups may be replaced by N,
c) a radical from the group consisting of 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, it being possible for the radicals a) and b) to be substituted by CN, Cl or F, preferably one or two times, $Z^1$ and $Z^2$, in each case independently of one another, are —CO—O—, —O—CO—, —$CH_2$O—, —O—$CH_2$—, —$CH_2CH_2$—, —CH=CH—, —C≡C— or a single bond, and
m is 0, 1 or 2, with the proviso that at least one of the groups $Y^2$, $Y^3$, Q and Q' is a radical containing at least one F atom.

The invention furthermore relates to the use of these compounds as components of liquid-crystalline media, and to liquid-crystal and electro-optical display elements which contain liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

One object of the invention is the provision of stable liquid-crystalline or mesogenic compounds which are suitable as components of liquid-crystalline media, in particular for TFT and STN displays.

The substances employed hitherto for this purpose all have certain disadvantages, for example inadequate stability to the action of heat, light or electrical fields, or unfavorable elastic and/or dielectric properties.

In particular in displays of the supertwist type (STN) having twist angles significantly greater than 220°, the materials employed hitherto have disadvantages.

It has now been found that the compounds of the formula I are eminently suitable as components of liquid-crystalline media. They can be used to obtain stable liquid-crystalline media, in particular suitable for TFT or STN displays. The novel compounds are distinguished, in particular, by high thermal stability, which is advantageous for a high holding ratio.

In addition, the provision of the compounds of the formula I very generally considerably broadens the range of liquid-crystalline substances which are suitable from various applicational points of view for the preparation of liquid-crystalline mixtures.

The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compound, in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystal display elements, in particular electro-optical display elements, which contain media of this type.

Above and below, $R^1$, $A^1$, $Z^1$, m, $A^2$, $Z^2$ and W have the defined meaning, unless expressly stated otherwise.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bco denotes a bicyclo(2,2,2)octylene radical, where Cyc and/or Phe may be unsubstituted or monosubstituted or polysubstituted by Cl, F or CN.

The compounds of the formula I include bicyclic compounds of the subformulae Ia and Ib:

$R^1$-$A^1$-W Ia
$R^1$-$A^2$-$Z^2$-W Ib

Tricyclic compounds of the subformulae Ic to If:

$R^1$-$A^1$-$A^2$-W Ic
$R^1$-$A^1$-$A^2$-$Z^2$-W Id
$R^1$-$A^1$-$Z^1$-$A^2$-W Ie
$R^1$-$A^1$-$Z^1$-$A^2$-$Z^2$-W If and tetracyclic compounds of the subformulae Ig to In:

$R^1$-$A^2$-$A^1$-$A^2$-W Ig
$R^1$-$A^1$-$Z^1$-$A^1$-$A^2$-W Ih
$R^1$-$A^1$-$A^1$-$Z^1$-$A^2$W Ii
$R^1$-$A^1$-$A^1$-$A^2$-$Z^2$W Ij
$R^1$-$A^1$-$Z^1$-$A^1$-$Z^1$-$A^2$-W Ik
$R^1$-$A^1$-$Z^1$-$A^1$-$A^2$-$Z^2$-W Il
$R^1$-$A^1$-$A^1$-$Z^1$-$A^2$-$Z^2$-W Im
$R^1$-$A^1$-$Z^1$-$A^1$-$A^2$-$A^2$-$Z^2$-W In

Of these, particular preference is given to those of the subformulae Ia, Ic, Id, Ie, Ig, Ih and Ii.

The preferred compounds of the subformula Ia include those of the subformulae Iaa and Iab:

$R^1$-Phe-W Iaa
$R^1$-Cyc-W Iab

The preferred compounds of the subformula Ib include those of the subformulae Iba and Ibb:

$R^1$-Phe-$Z^2$-W Iba
$R^1$-Cyc-$Z^2$-W Ibb

The preferred compounds of the subformula Ic include those of the subformulae Ica to Icg:

$R^1$Cyc-Cyc-W Ica
$R^1$-Cyc -Phe-W Icb
$R^1$-Phe-Phe-W Icc
$R^1$-Pyd-Phe-W Icd
$R^1$-Phe-Cyc-W Ice
$R^1$-Dio-Phe-W Icf
R-Pyr-Phe-W Icg

Of these, those of the formulae Ica, Icb, Icc and Ice are particularly preferred.

The preferred compounds of the subformula Id include those of the subformulae Ida to Idg:

$R^1$-Cyc-Cyc-$Z^2$-W Ida
$R^1$-Cyc-Phe-$Z^2$-W Idb
$R^1$-Phe-Phe-$Z^2$-W Idc
$R^1$-Pyr-Phe-$Z^2$-W Idd
$R^1$-Pyd-Phe-$Z^2$-W Ide
$R^1$-Cyc-Phe-$CH_2CH_2$-W Idf
$R^1$-$A^1$-Phe-$CH_2CH_2$-W Idg

The preferred compounds of the subformula Ie include those of the subformulae Iea to Ieh:

$R^1$-Cyc-$Z^1$-Cyc-W Iea
$R^1$-$A^1$-$CH_2CH_2$-$A^2$-W Ieb
$R^1$-Cyc-$Z^1$-Phe-W Iec
$R^1$-$A^1$-OCO-Phe-W Ied
$R^1$-Phe-$Z^1$-Phe-W Iee
$R^1$-Pyr-$Z^1$-$A^2$-W Ief
$R^1$-Pyd-$Z^1$-$A^2$-W Ieg
$R^1$-Dio-$Z^1$-$A^2$-W Ieh

Of these, those of the subformulae Iea, Ieb, Iec and Iee are particularly preferred.

The preferred compounds of the subformula If include those of the subformulae Ifa to Ife:

$R^1$-Phe-$CH_2CH_2$-$A^2$-$Z^2$-W Ifa
$R^1$-$A^1$-COO-Phe-$Z^2$-W Ifb
$R^1$-Cyc-$Z^1$-Cyc-$Z^2$-W Ifc
$R^1$-Phe-$Z^1$-Phe-$Z^2$-W Ifd
$R^1$-Cyc-$CH_2CH_2$-Phe-$Z^2$-W Ife

The preferred compounds of the subformulae Ig to In include those of the subformulae Io to Iv:

$R^1$-$A^1$-Cyc-Cyc-W Io
$R^1$-$A^1$-Cyc-Phe-W Ip
$R^1$-$A^1$-$CH_2CH_2$-$A^1$-Phe-W Iq
$R^1$-Cyc-$Z^1$-$A^1$-$Z^1$-Phe-W Ir
$R^1$-Phe-Phe-Phe-W Is
$R^1$-Phe-$Z^1$-$A^1$-Phe-W It
$R^1$-$A^1$-Phe-$Z^1$-Phe-W Iu
$R^1$-$A^1$-$Z^1$-Cyc-Phe-$Z^2$-W Iv

In the compounds of the formulae above and below, $R^1$ is preferably alkyl, furthermore preferably alkoxy.

$A^1$ and $A^2$, independently of one another, are preferably Phe, Cyc, Che, Pyd, Pyr or Dio. The compounds of the formula I preferably contain not more than one of the radicals Bco, Pyd, Pyr, Dio and Dit.

If the ring $A^1$ is present twice, the two rings may have identical or different meanings. The same also applies to the bridge $Z^1$.

Preference is also given to compounds of the formula I and to all subformulae in which $A^1$ and/or $A^2$ is 1,4-phenylene which is monosubstituted or disubstituted by F or CN.

m is preferably 0 or 1, particularly preferably 1. X is preferably H or F, particularly preferably H. $Z^1$ and $Z^2$, independently of one another, are preferably —$CH_2CH_2$—, —CO—O—, —O—CO— or a single bond, particularly preferably a single bond.

In the structural element W, $A^3$ is preferably a cyclohexane or phenyl ring, particularly preferably a phenyl ring.

The 1,4-cyclohexenylene group preferably has the following structures:

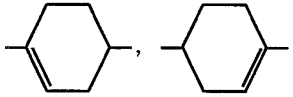

$Y^1$ is preferably O, and $Y_2$ is O, $CF_2$ or S, particularly preferably O or $CF_2$.

Q is preferably $CF_2$, C=O, $CFR^2$ or $CHR^2$, particularly preferably $CF_2$ or C=O.

If Q is C=O, CHF or $CF_2$, $Y^2$ is preferably also $CHR^2$ or $CFR^2$.

Q' is CF or $CR^2$, preferably $CR^2$.

$Y^3$ is preferably N or CF. If Q' is CF, $Y^3$ is preferably also $CR^2$.

At least one of the groups $Y^2$, $Y^3$, Q and Q' is a radical containing at least one F atom, so that the five-membered ring always carries at least one fluorine atom.

$R^2$ is preferably an alkyl radical having 1–7 carbon atoms which is unsubstituted or monosubstituted by at least one F atom. Particular preference is given to the radicals methyl, trifluoromethyl, ethyl, pentafluoroethyl, propyl, heptafluoropropyl, monofluoromethyl, difluoromethyl, butyl, pentyl, hexyl or heptyl.

The formulae 1–12 represent particularly preferred meanings of the structural elements W:

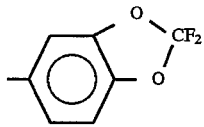 (1)

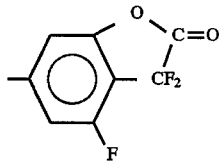 (2)

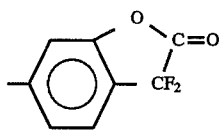 (3)

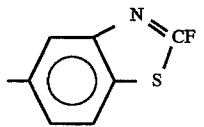 (4)

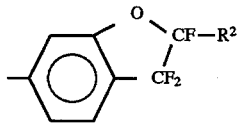 (5)

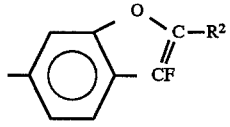 (6)

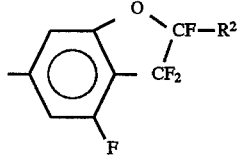 (7)

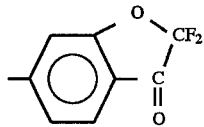 (8)

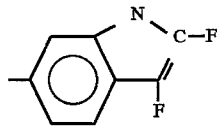 (9)

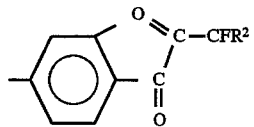 (10)

-continued

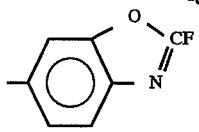 (11)

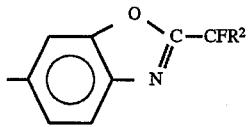 (12)

If $R^1$ in the formulae above and below is an alkyl radical and/or an alkoxy radical, it may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxa-nonyl, or 2-, 3-, 4-, 5-, 6-, 7-, 8- or 9-oxadecyl.

If $R^1$ is an alkyl radical in which one $CH_2$ group has been replaced by —CH=CH—, it may be straight-chain or branched. It is preferably straight-chain and has 2 to 10 carbon atoms. Accordingly, it is in particular vinyl, prop-1- or 2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one $CH_2$ group has been replaced by —O— and one by —CO—, these are preferably adjacent. These thus contain an acyloxy group —CO—O— or an oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-propoxycarbonyl)ethyl, 3-(methoxycarbonyl)propyl, 3-(ethoxycarbonyl)propyl or 4-(methoxycarbonyl)butyl.

If $R^1$ is an alkyl radical in which one $CH_2$ group has been replaced by unsubstituted or substituted —CH=CH— and an adjacent $CH_2$ group has been replaced by CO or CO—O or O—CO—, it may be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If $R^1$ is an alkyl or alkenyl radical which is monosubstituted by CN or $CF_3$, this radical is preferably straight-chain and the substitution by CN or $CF_3$ is in the ω-position.

If $R^1$ is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent can be in any desired position, but is preferably in the ω-position.

Compounds of the formula I containing a branched wing group $R^1$ may occasionally be of importance due to better solubility in the conventional liquid-crystalline base materials, but in particular as chiral dopes if they are optically active. Smectic compounds of this type are suitable as components of ferroelectric materials.

Branched groups of this type generally contain not more than one chain branch. Preferred branch radicals $R^1$ are isopropyl, 2-butyl (=1-methylpropyl, isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers the racemates of these compounds and the optical antipodes, and mixtures thereof.

Of these compounds of the formula I and the subformulae, those are preferred in which at least one of the radicals present therein has one of the preferred meanings indicated.

In the compounds of the formula I, preferred stereoisomers are those in which the rings Cyc and piperidine are trans-1,4-disubstituted. Those of the abovementioned formulae which contain one or more groups Pyd, Pyr and/or Dio in each case include the two 2,5-positional isomers.

Some very particularly preferred smaller groups of compounds of the formula I are those of the subformulae I1 to I12:

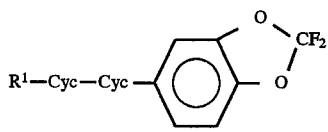 I1

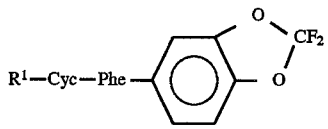 I2

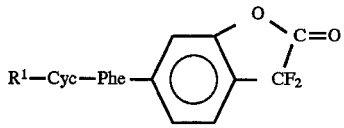 I3

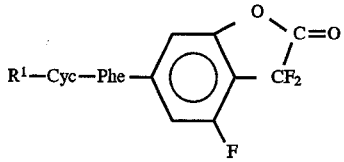 I4

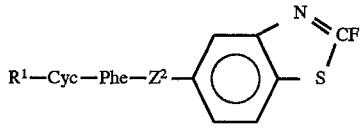 I5

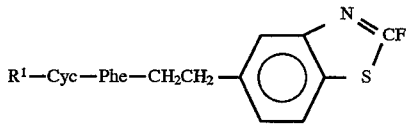 I6

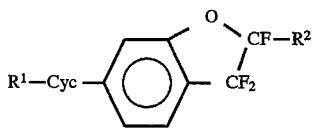 I7

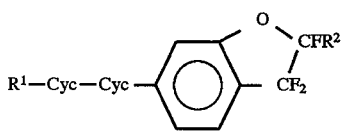 I8

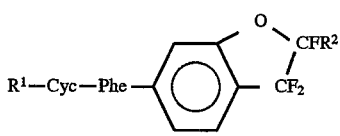 I9

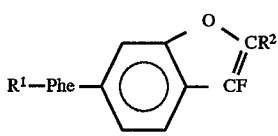 I10

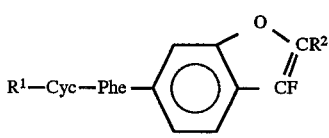 I11

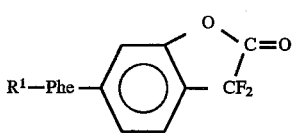 I12

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions.

Use may also be made here of variants which are known per se, but are not mentioned here in greater detail.

If desired, the starting materials can also be formed in situ by not isolating them from the reaction mixture, but instead immediately converting them further into the compounds of the formula I.

The compounds according to the invention can be prepared, for example, in accordance with the reaction schemes below:

Scheme 1
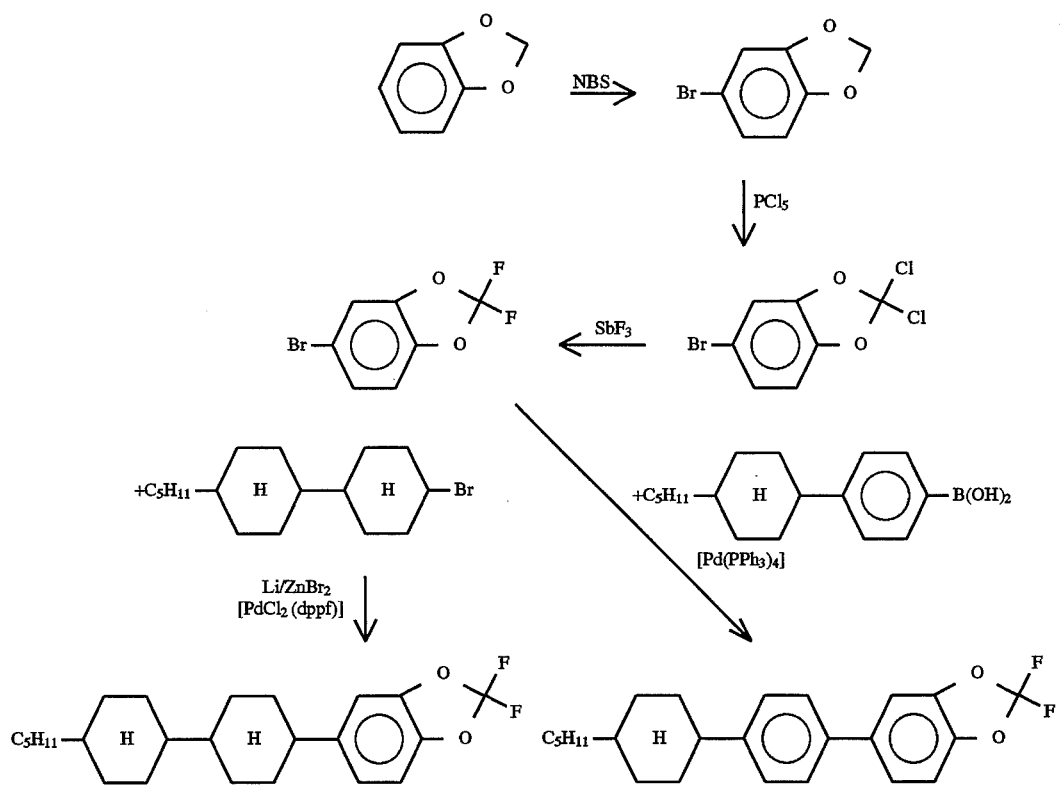
NBS = N-bromosuccinimide
dppf = diphenylphosphinoferrocene
Scheme 2
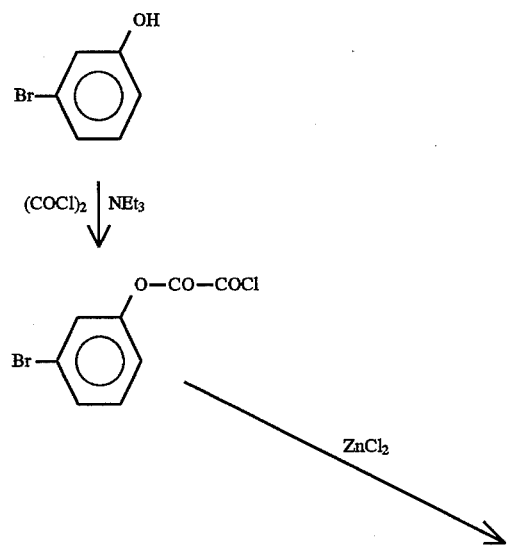

-continued
Scheme 2

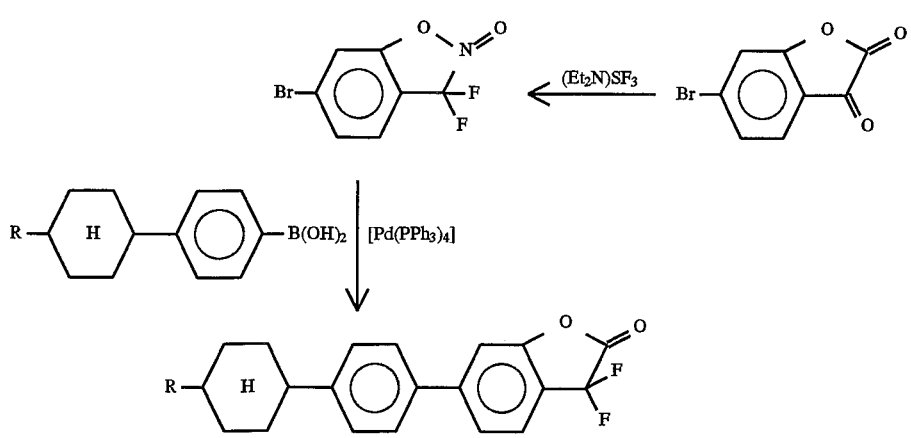

Esters of the formula I can also be obtained by esterifying corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

In a further process for the preparation of the compounds of the formula I in which $Z^1$ or $Z^2$ is —CH=CH—, an aryl halide is reacted with an olefin in the presence of a tertiary amine and a palladium catalyst (cf. R. F. Heck, Acc. Chem. Res. 12 (1979) 146). Examples of suitable aryl halides are chlorides, bromides and iodides, in particular bromides and iodides. The tertiary. amines necessary for the success of the coupling reaction, such as, for example, triethylamine, are also suitable as solvents. Examples of suitable palladium catalysts are salts thereof, in particular Pd(II) acetate, and organophosphorus(III) compounds, such as, for example, triarylphosphines. The process can be carried out in the presence or absence of an inert solvent at temperatures between about 0° and 150°, preferably between 20° and 100°; examples of suitable solvents are nitriles, such as acetonitrile, or hydrocarbons, such as benzene or toluene. The aryl halides and olefins employed as starting materials are frequently commercially available or can be prepared by processes known from the literature, for example by halogenation of corresponding parent compounds or by elimination reactions on corresponding alcohols or halides.

In this way, stilbene derivatives, for example, can be prepared. The stilbenes can also be prepared by reacting a 4-substituted benzaldehyde with an appropriate phosphorus ylide by the Wittig method. However, tolans of the formula I can also be prepared by replacing the olefin by monosubstituted acetylene (Synthesis 627 (1980) or Tetrahedron Lett. 27, 1171 (1986)).

Coupling of aromatic compounds can furthermore be effected by reacting aryl halides with aryltin compounds. These reactions are preferably carried out with addition of a catalyst, such as, for example, a palladium(0) complex, in inert solvents, such as hydrocarbons, at high temperatures, for example in boiling xylene, under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which $Z^1$ or $Z^2$ is —C≡C— can also be prepared by the Fritsch-Buttenberg-Wiechell rearrangement (Ann. 279, 319, 1984), in which 1,1-diaryl-2-haloethylenes are rearranged in the presence of strong bases to give diarylacetylenes.

Tolans of the formula I can also be prepared by brominating the corresponding stilbenes and subsequently dehydrohalogenating the bromination product. Use may also be made here of variants which are known per se, but are not mentioned here in greater detail.

Ethers of the formula I are obtainable by etherifying corresponding hydroxyl compounds, preferably corresponding phenols, the hydroxyl compound expediently first being converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This can then be reacted with the appropriate alkkyl halide, sulphonate or dialkyl sulphate, expediently in an inert solvent, such as, for example, acetone, 1,2-dimethoxyethane, DMF or dimethyl sulphoxide, or else with an excess of aqueous or aqueous/alcoholic NaOH or KOH, at temperatures between about 20° and 100°.

The starting materials are either known or can be prepared analogously to known compounds.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)- ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-CH$_2$zCH$_2$-E-R" | 4 |
| R'-L-C≡C-E-R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In a smaller subgroup of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller subgroup is called group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller subgroup of the compounds of the formulae 1, 2, 3, 4 and 5 which is known as group B, R" is —F, —Cl, —NCS or —(O)$_i$CH$_{3-(k+l)}$F$_k$Cl$_l$, where i is 0 or 1, and k+l is 1, 2 or 3; the compounds in which R" has this meaning are labelled with the subformulae 1b, 2b, 3b, 4b and 5b. Particular preference is given to those compounds of the subformulae 1b, 2b, 3b, 4b and 5b in which R" is —F, —Cl, —NCS, —CF$_3$, —OCHF$_2$ or —OCF$_3$.

In the compounds of the subformulae 1b, 2b, 3b, 4b and 5b, R' is as defined for the compounds of the subformulae 1a–5a and is preferably alkyl, alkenyl, alkoxy or alkoxyalkyl.

In a further smaller subgroup of the compounds of the formulae 1, 2, 3, 4 and 5, R" is —CN; this sub-group is known as group C below, and the compounds of this subgroup are correspondingly described by sub-formulae 1c, 2c, 3c, 4c and 5c. In the compounds of the subformulae 1c, 2c, 3c, 4c and 5c, R' is as defined for the compounds of the subformulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably contain one or more compounds selected from group A and/or group B and/or group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5%–90% and in particular 10% to 90%.

The media according to the invention preferably contain 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the alignment of the nematic phases.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight. mp.=melting point, cp.=clearing point. Furthermore, C=crystalline state, N=nematic phase, S=smectic phase and I=isotropic phase. The data between these symbols represent the transition temperatures. An denotes the optical anisotropy (589 nm, 20° C.), and the viscosity (mm$^2$/sec) was determined at 20° C.

The entire disclosure of all applications, patents, and publications, cited above and below, including German application number P 42 00 524, filed Jan. 11, 1992, are hereby incorporated by reference.

"Conventional work-up" means that water is added if necessary, the mixture is extracted with methylene chloride, diethyl ether or toluene, the organic phase is separated off, dried and evaporated, and the product is purified by distillation under reduced pressure or crystallisation and/or chromatography.

The following abbreviations are used: NBS N-bromosuccinimide PdCl$_2$ (dppf) (diphenylphosphinoferrocene)palladium dichloride PE petroleum ether THF tetrahydrofuran

EXAMPLES

Example 1 a) 0.487 mol of 1,2-methylenedioxybenzene and 0.512 mol of NBS are refluxed together for three hours in 250 ml of CHCl$_3$.

The reaction solution is left to stand overnight and is then evaporated. The residue is taken up in PE/H$_2$O, washed with H$_2$O, dried, filtered through silica gel and evaporated on a rotary evaporator. The residue is distilled, giving 1,2-methylenedioxy-4-bromobenzene.

b) 30 mmol of 1,2-methylenedioxy-4-bromobenzene are heated to 90° C. together with 30 mmol of PCl$_5$, and, when the evolution of gas is complete, the mixture is stirred for a further hour. Purification by distillation gives 1,2-dichloromethylenedioxy-4-bromobenzene.

This compound is converted into 1,2-difluoromethylenedioxy-4-bromobenzene by reaction with SbF$_3$ in dioxane.

c) A mixture of 0.075 mol of trans-4-(trans-4-pentylcyclohexyl)cyclohexyl bromide, 0.180 mol of lithium, 0.030 mol of ZnBr$_2$ and 150 ml of THF/toluene (¼) is treated with ultrasound for 2 hours at 5° C. under a nitrogen atmosphere.

0.06 mol of 1,2-difluoromethylenedioxy-4-bromobenzene and 1.05 g of PdCl$_2$ (dppf) are then added. The mixture is stirred at 5° C. for 2 hours and at room temperature overnight. Evaporation on a rotary evaporator and filtration through silica gel (PE) gives, after chromatographic purification, 1,2-(difluoromethylenedioxy)-4-[trans-4-(trans-4-pentylcyclohexyl)cyclohexyl]benzene having C 77° N 93.6° I.

Examples 2 to 14

The following compounds according to the invention are obtained analogously to Example 1 from the corresponding precursors:

| | R$^1$ | A$^1$ | A$^2$ | W |
|---|---|---|---|---|
| (2) | Ethyl | Cyc | Cyc | phenyl-OCF$_2$O |
| (3) | n-Propyl | Cyc | Cyc | phenyl-OCF$_2$O |
| (4) | n-Butyl | Cyc | Cyc | phenyl-OCF$_2$O |
| (5) | n-Hexyl | Cyc | Cyc | phenyl-OCF$_2$O |
| (6) | n-Heptyl | Cyc | Cyc | phenyl-OCF$_2$O |
| (7) | Ethyl | Phe | Cyc | phenyl-OCF$_2$O |
| (8) | n-Propyl | Phe | Cyc | phenyl-OCF$_2$O |
| (9) | Methyl | Cyc | Cyc | phenyl-OCF$_2$O |
| (10) | Methyl | Phe | Cyc | phenyl-OCF$_2$O |
| (11) | n-Butyl | Phe | Cyc | phenyl-OCF$_2$O |
| (12) | n-Pentyl | Phe | Cyc | phenyl-OCF$_2$O |
| (13) | n-Hexyl | Phe | Cyc | phenyl-OCF$_2$O |
| (14) | n-Heptyl | Phe | Cyc | phenyl-OCF$_2$O |

Example 15

A mixture of 0.043 mol of (trans-4-pentylcyclohexyl) phenylboronic acid, 0.043 mol of 1,2-difluoromethylenedioxy-4-bromobenzene (prepared as described in Example 1a–b), 75 ml of toluene, 37.5 ml of EtOH, 0.086 mol of $Na_2CO_3 \cdot 10H_2O$ +24 ml of $H_2O$ and 0.53 g of $Pd(PPh_3)_4$ is refluxed for 20 hours then subjected to customary work-up by means of PE. Purification on silica gel (hexane) gives 1,2-(difluoromethylenedioxy)-4-[4-(trans-4-pentylcyclohexyl)phenyl]benzene having C 69° N 81° I.

Examples 16–29

The following compounds according to the invention are obtained analogously to Example 15 from the corresponding precursors:

| | $R^1$ | $A^1$ | $A^2$ | W |
|---|---|---|---|---|
| (16) | Ethyl | Cyc | Phe |  |
| (17) | Methyl | Cyc | Phe |  |
| (18) | n-Propyl | Cyc | Phe |  |
| (19) | n-Butyl | Cyc | Phe | 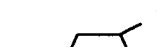 |
| (20) | n-Hexyl | Cyc | Phe |  |
| (21) | n-Heptyl | Cyc | Phe | 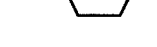 |
| (22) | n-Octyl | Cyc | Phe | 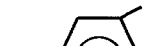 |
| (23) | Methyl | Phe | Phe |  |
| (24) | Ethyl | Phe | Phe |  |
| (25) | n-Propyl | Phe | Phe | 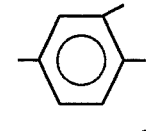 |
| (26) | n-Butyl | Phe | Phe | 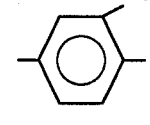 |
| (27) | n-Pentyl | Phe | Phe | 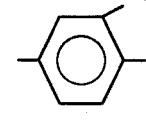 |
| (28) | n-Hexyl | Phe | Phe | 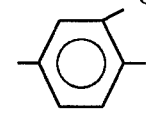 |
| (29) | n-Heptyl | Phe | Phe | 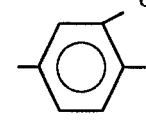 |

Examples 30–59

The following compounds according to the invention are obtained analogously to Examples 1 or 15 from the corresponding precursors:

| | $R^1$ | $A^1$ | $A^2$ | W |
|---|---|---|---|---|
| (30) | Methyl | — | Cyc | 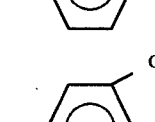 |
| (31) | Ethyl | — | Cyc |  |
| (32) | n-Propyl | — | Cyc | 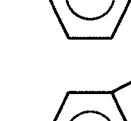 |
| (33) | n-Butyl | — | Cyc |  |
| (34) | n-Pentyl | — | Cyc |  |

| | R¹ | A¹ | A¹ | A² | W |
|---|---|---|---|---|---|
| (35) | n-Hexyl | — | — | Cyc | benzodioxole-CF₂ |
| (36) | n-Heptyl | — | — | Cyc | benzodioxole-CF₂ |
| (37) | Methyl | — | — | Phe | benzodioxole-CF₂ |
| (38) | Ethyl | — | — | Phe | benzodioxole-CF₂ |
| (39) | n-Propyl | — | — | Phe | benzodioxole-CF₂ |
| (40) | n-Butyl | — | — | Phe | benzodioxole-CF₂ |
| (41) | n-Pentyl | — | — | Phe | benzodioxole-CF₂ |
| (42) | n-Hexyl | — | — | Phe | benzodioxole-CF₂ |
| (43) | Ethyl | Phe | Cyc | Cyc | benzodioxole-CF₂ |
| (44) | n-Propyl | Phe | Cyc | Cyc | benzodioxole-CF₂ |
| (45) | n-Butyl | Phe | Cyc | Cyc | benzodioxole-CF₂ |

| | R¹ | A¹ | A¹ | A² | W |
|---|---|---|---|---|---|
| (46) | n-Pentyl | Phe | Cyc | Cyc | benzodioxole-CF₂ |
| (47) | n-Hexyl | Phe | Phe | Cyc | benzodioxole-CF₂ |
| (48) | n-Heptyl | Phe | Phe | Cyc | benzodioxole-CF₂ |
| (49) | n-Pentyl | Phe | Phe | Phe | benzodioxole-CF₂ |
| (50) | n-Butyl | Phe | Phe | Phe | benzodioxole-CF₂ |
| (51) | Ethyl | Cyc | Cyc | Phe | benzodioxole-CF₂ |
| (52) | n-Propyl | Cyc | Cyc | Phe | benzodioxole-CF₂ |
| (53) | n-Butyl | Cyc | Cyc | Phe | benzodioxole-CF₂ |
| (54) | n-Pentyl | Cyc | Cyc | Phe | benzodioxole-CF₂ |
| (55) | Ethyl | Phe | Cyc | Phe | benzodioxole-CF₂ |
| (56) | n-Propyl | Phe | Cyc | Phe | benzodioxole-CF₂ |

-continued

| R¹ | A¹ | A¹ | A² | W |
|---|---|---|---|---|
| (57) n-Pentyl | Phe | Cyc | Phe | 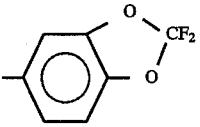 |
| (58) n-Pentyl | Cyc | Cyc | Cyc | 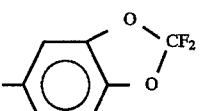 |
| (59) n-Butyl | Cyc | Cyc | Cyc | 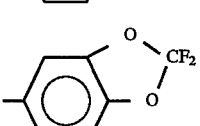 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An achiral fluorine-containing five-membered ring compound of formula I $$R^1\text{-}(A^1\text{-}Z^1)_m\text{-}A^2\text{-}Z^2\text{-}W \quad I$$

in which

W is

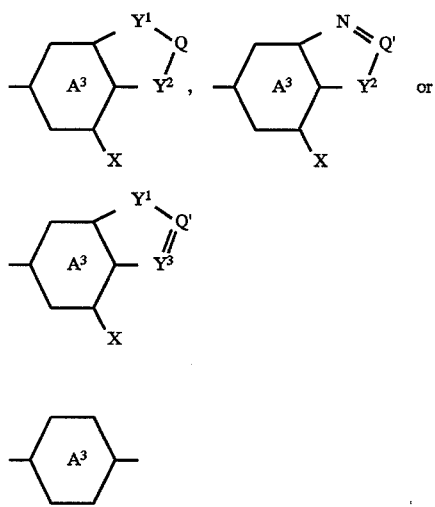

$A^3$ is a cyclohexane, cyclohexene or phenyl ring, $Y^1$ is O or S, $Y^2$ is (a) O, C=O or $CH_nF_{2-n}$, or (b) if Q is C=O, CHF or $CF_2$, $Y^2$ may additionally be $CHR^2$ or $CFR^2$, n is 0, 1 or 2, $Y^3$ is (a) N, CH or CF, or (b) if Q' is CF, $Y^3$ may alternatively be $CR^2$, Q is C=O, CHF, $CF_2$, $CHR^2$ or $CFR^2$, A' is CF or $CR^2$, $R^2$ is $C_{1-15}$-alkyl, optionally at least monosubstituted by F, X is H, F or Cl, $R^1$ is alkyl or alkenyl having 1–15 carbon atoms which is optionally monosubstituted by CN or $CF_3$ or at least monosubstituted by halogen, at least one CH group optionally independently being replaced by —O—, —S—, —CO—,

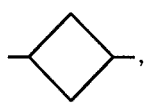

—CO—O—, —O—CO or —O—CO—O— in such a manner that heteroatoms are not linked directly to one another, $A^1$ and $A^2$ are each independently a) a trans-1,4-cyclohexylene radical in which one or more non-adjacent $CH_2$ groups are optionally replaced by —O— and/or —S—, b) a 1,14-phenylene radical in which one or two CH groups are optionally replaced by N, c) 1,4-cyclohexyenylene, 1,4-bicyclo(2,2,2)-octylene, piperidine-1,4-diyl, naphthalene-2,6-diyl, decahydronaphthalene-1,6-diyl or 1,2,3,4-tetrahydronaphthalene-2,6-diyl, and in which the radicals a) and b) are optionally substituted by CN, Cl or F, $Z^1$ and $Z^2$ are each independently —CO—O—, —O—CO—, —$CH_2$—O—, —O—$CH_2$—, —$CH_2CH_2$—, —CH=CH—, —C≡C— or a single bond, and m is 0, 1 or 2, with the provisos that at least one of the groups $Y^2$, $Y^3$ Z and Q' is a radical containing at least one F atom, and that $Y^2$ is different from Q.

2. A liquid crystalline medium having at least two liquid-crystalline components, wherein at least one component is a compound of of claim 1 according to formula I.

3. A liquid-crystal display element, containing a liquid-crystalline medium according to claim 2.

4. An electro-optical display element, containing a dielectric which is a liquid-crystalline medium according to claim 2.

5. A compound according to claim 1 wherein $R^2$ is straight-chain $C_{1-15}$-alkyl, optionally at least mono-substituted by F.

6. A compound according to claim 1, wherein $R^2$ is straight-chain $C_{1-15}$-alkyl.

7. A compound according to claim 1, wherein $R^1$ is straight-chain alkyl or straight-chain alkenyl having 1–15 carbon atoms which is optionally monosubstituted by CN or $CF_3$ or at least monosubstituted by halogen, at least one $CH_2$ group optionally independently being replaced by —O—, —S—, —CO—,

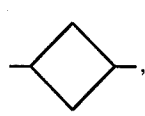

—CO—O—, —O—CO— or —O—CO—O— in such a manner that heteroatoms are not linked directly to one another.

8. In a nematic liquid crystalline mixture, comprising at least two liquid crystalline components, the improvement wherein at least one component is a compound according to claim 1.

9. A liquid crystalline display according to claim 3, based on the TFT or STN effect.

10. An achiral liquid crystalline mixture having at least two liquid crystalline components, wherein at least one component is a compound of formula I $R^1-(A^1Z^1)_m-A^2-Z^2-W$   I in which W is

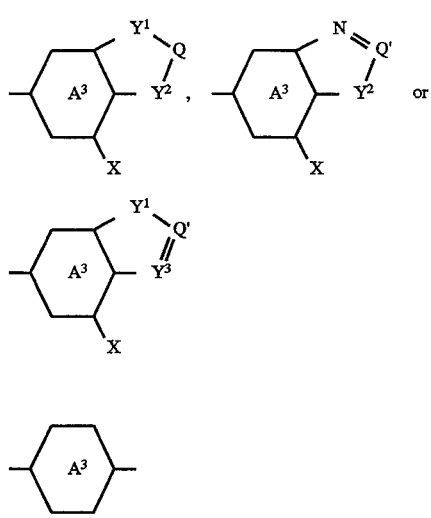

is a cyclohexane, cyclohexene or phenyl, $Y^1$ is O or S, $Y^2$ is (a) O, C=O or $CH_nF_{2-n}$, or (b) if Q is C=O, CHF or $CF_2$, $Y^2$ may additionally be $CHR^2$ or $CFR^2$, n is 0, 1 or 2, $Y^3$ is (a) N, CH or CF, or (b) of Q' is CF, $Y^3$ may alternatively be $CR^2$, Q is C=O, CHF, $CF_2$, $CHR^2$ or $CFR^2$, Q' is CF or $CR^2$, $R^2$ is $C_{1-15}$-alkyl, optionally at least mono-substituted by F, X is H, F or Cl, $R^1$ is H, alkyl or alkenyl having 1–15 carbon atoms which is optionally monosubstituted by CN or $CF_3$ or at least monosubstituted by halogen, at lease one $CH_2$ group optionally independently being replaced by —O—, —S—, —CO—,

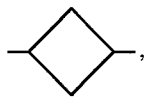

—CO—O—, —O—CO— or —O—CO—O— in such a manner that heteroatoms are not linked directly to one another, $A^1$ and $A^2$ are each independently
  a) a trans-1,4-cyclohexylene radical in which one or more non-adjacent $CH_2$ groups are optionally replaced by —O— and/or —S—,
  b) a 1,4-phenylene radical in which one or two CH groups are optionally replaced by N,
  c) 1,4-cyclohexyenylene, 1,4-bicyclo(2,2,2)-octylene, piperidine-1,4-diyl, naphthalene-2,6-diyl, decahydronaphthalene-2,6-diyl or 1,2,3,4-tetrahydronaphthalene-2,6-diyl, and which the radicals a) and b) are optionally substituted by CN, Cl or F, $Z^1$ and $Z^2$ are each independently —CO—O, —O—CO—, —$CH_2$O—, —O—$CH_2$—, —$CH_2CH_2$—, —CH=CH—, —C≡C— or a single bond, and m is 0, 1 or 2, with the provisos that at least one of the groups $Y^2$, $Y^3$, Q and Q' is a radical containing at least one F atom, and that $Y^2$ is different from Q.

* * * * *